United States Patent [19]

Cisneros

[11] Patent Number: 5,430,215
[45] Date of Patent: Jul. 4, 1995

[54] SELECTIVE HYDRODECHLORINATION OF 1,2,3-TRICHLOROPROPANE TO PRODUCE PROPYLENE

[75] Inventor: Mark D. Cisneros, Baton Rouge, La.

[73] Assignee: The Dow Chemical Company, Midland, Mich.

[21] Appl. No.: 227,839

[22] Filed: Apr. 14, 1994

[51] Int. Cl.[6] .................. C07C 1/02; C07C 5/327; C07C 5/373
[52] U.S. Cl. .................. 585/642; 585/638; 585/641; 585/654; 585/657; 585/660
[58] Field of Search .............. 585/638, 641, 642, 654, 585/657, 660

[56] References Cited

U.S. PATENT DOCUMENTS 2,886,605  5/1959  McClure et al. .
3,927,131  12/1975  Ward .................. 570/227
4,384,159  5/1983  Diesen .................. 585/642
5,105,032  4/1992  Holbrook et al. .

FOREIGN PATENT DOCUMENTS 015665  2/1980  European Pat. Off. .
0253410  7/1987  European Pat. Off. .
0459463  5/1991  European Pat. Off. .
5231005  9/1975  Japan .
5320076  12/1993  Japan .
1400529  12/1972  United Kingdom .

Primary Examiner—Asok Pal
Assistant Examiner—E. D. Irzinski

[57] ABSTRACT

A process for hydrodechlorinating 1,2,3-trichloropropane to produce propylene in preference to propane, comprising reacting 1,2,3-trichloropropane and hydrogen in the presence of a Group VIII metal on carbon catalyst, and especially a platinum on carbon catalyst.

9 Claims, No Drawings

SELECTIVE HYDRODECHLORINATION OF 1,2,3-TRICHLOROPROPANE TO PRODUCE PROPYLENE

This invention relates generally to hydrodechlorination processes and catalysts, and more particularly to the hydrodechlorination of 1,2,3-trichloropropane (hereafter, TCP) to produce propylene.

The material TCP is a significant byproduct of epichlorohydrin production from allyl chloride. TCP has some commercial uses, but in light of the increasing regulatory pressure on chlorinated hydrocarbons like TCP and on the incineration of such, it has become increasingly attractive to in some way extract the carbon value from TCP and reduce the incineration requirements associated with this material.

The present invention accordingly provides a process for catalytically selectively hydrodechlorinating TCP to propylene in yields of at least 10 percent, but preferably at least 20 percent and more preferably at least 30 percent (where the yield is defined as the selectivity to propylene multiplied by the conversion of the TCP, on an hydrogen chloride- and hydrogen-free basis), wherein TCP is reacted with hydrogen in the presence of a catalyst which consists essentially of a Group VIII metal in elemental or compound form on a support under conditions selected to favor the production of propylene over propane (where the Group VIII metals are those denominated as such in the Periodic Table of the Elements produced by Sargent-Welch Scientific Co., Skokie, Ill. (Cat. No. S-18806, copyright 1979), namely, iron, cobalt, nickel, ruthenium, rhodium, palladium, osmium, iridium and platinum). A platinum on carbon catalyst is particularly preferred.

Other hydrodechlorination catalysts and processes are of course known in the art. Certain of these processes apparently relate exclusively to chlorofluorocarbon starting materials. European Patent Application EP 0496446A, for example, describes the preparation of chlorotrifluoroethylene and trifluoroethylene from 1,1,2-trichloro-1,2,2-trifluoroethane via a catalyst comprised of copper and a Group VIII or noble metal (palladium and platinum being preferred) on a carbon support. Several prior publications address the same conversion and describe the same or different catalysts, see, for example EP 0253410B, EP 0355907B and EP 0459463A.

A seemingly separate course of development has occurred with respect to the class of chlorinated hydrocarbon feedstocks which are exclusive of the chlorofluorocarbon feedstocks. For example, EP 015665 describes the conversion of 1,1,2-trichloroethane to ethylene or to vinyl chloride via a catalyst including a noble metal chloride, an alkali metal chloride, iron chloride and optionally copper chloride on a silica or alumina support. An earlier Japanese patent publication JP 77/31005 which is referenced in the EP 015665 publication relates to the same overall process, but employs a catalyst of palladium chloride, copper chloride and an alkali metal chloride on a support.

U.S. Pat. No. 2,886,605 to McClure et al. describes processes for reducing the chlorine or bromine content of halohydrocarbons containing one or both of these halogens via a cuprous halide on porous active alumina catalyst. Specifically contemplated are processes for converting 1,2-dichloropropane to propylene and hydrogen chloride, for converting perchloroethylene to trichloroethylene, and for converting 1,1,2-trichloroethane to vinyl chloride.

British patent GB 1,400,529 to Scharfe broadly relates to processes for converting byproduct and waste "hydrocarbon chlorides" to "chlorine-free hydrocarbons" via a rhodium-containing catalyst, and specifically describes the conversion of 1,2-dichloropropane to propane, as well as describing the conversion of chloropropane to propylene. Combinations of rhodium with other metals or metal compounds are contemplated, those being named including palladium, platinum, ruthenium, iridium, iron, cobalt, nickel, copper, gold, vanadium, chromium, molybdenum or tungsten, and the salts, hydroxides, oxides or carboxylates of the alkali and alkaline earth metals.

Other known references are more specifically addressed to the conversion of 1,2-dichloropropane (a co-product of the manufacture of propylene oxide by a chlorohydrin process) to propylene.

In German Patent Publication No. 235,630 A1, for example, 1,2-dichloropropane is converted to propylene in a catalytic gas phase reaction at temperatures ranging from 170 degrees Celsius to 450 degrees Celsius. The catalyst is described as an activated carbon which has been treated with a suspension of iron oxides and/or iron oxide hydrates, and then dried at temperatures in the range of 80 degrees to 200 degrees Celsius.

Other methods described in this publication include the conversion (preferably at 180–250 degrees Celsius) in the presence of hydrogen and of a rhodium catalyst of 1,2-dichloropropane to propylene, the dechlorination at normal temperatures of 1,2-dichloropropane to a mixture (9:1) of propylene and chloropropylene in the presence of a pure titanium catalyst, and the reductive dehalogenation with sodium sulfide and a phase transfer catalyst of chlorinated hydrocarbons to alkylenes. The production of alkylenes from halogenated phosphonate esters under the influence of sulfur and olefinating agents containing phosphorus is also described.

None of these references, however, appears to show or alone or in combination to suggest the process of the present invention for effectively and selectively hydrodechlorinating TCP to propylene, which can for example be recycled to the allyl chloride process for producing additional allyl chloride for epichlorohydrin manufacture.

By a preferred embodiment, as has been indicated previously, TCP is reacted with hydrogen in the presence of a platinum on carbon catalyst to produce propylene in a yield of at least 10 percent, but preferably yielding about 20 percent and most particularly about 30 percent, under conditions favoring the production of propylene over propane. These conditions have in a preferred gas phase process (a liquid process also being generally contemplated, however) been found generally to correspond with lower pressures, for example, about 1000 psig or less, especially about 250 psig or less and most especially about 100 psig or less, and low hydrogen to TCP ratios of about 10 to 1 or less, especially about 5 to 1 or less and most especially about 1 to 1 or less. Higher hydrogen to TCP ratios than these have generally been found to preferentially produce propane and to be associated with undesirably high rates of catalyst deactivation, but at these relatively low hydrogen to TCP feed ratios the per-pass conversion can be low, so that a staged addition of hydrogen is generally considered desirable. Such staged hydrogen addition may optionally and preferably be accompanied also by the addition in the feed to the process of a high heat capacity inert, such as methane, to moderate the rate of reaction and generation of heat therefrom.

Corresponding reaction temperatures can range from about 25 degrees Celsius to about 400 degrees Celsius, with residence times being from about 0.1 seconds to about 7,200 seconds. Preferred temperatures will be from about 150 degrees Celsius to about 350 degrees Celsius and more preferably will be from about 150 degrees Celsius to about 250 degrees Celsius, with residence times of from about 0.1 seconds to about 30 seconds and especially from about 0.5 seconds to about 20 seconds.

Preferably the platinum-on-carbon catalyst will have been pretreated by exposure to a chloride source in the manner of U.S. Pat. No. 5,105,032 to Holbrook et al., so that the catalyst is not exposed to the TCP and hydrogen without the presence of a chloride source. The purpose of a chloride source pretreatment of the catalyst is fundamentally the same as in the aforementioned U.S. Pat. No. No. 5,105,032 to Holbrook et al.—namely, the amelioration or prevention of the significant coking and relatively high rates of catalyst deactivation which can be expected of these highly active catalysts in the absence of a chloride source pretreatment and the maintenance of a chloride source presence.

Finally, it will be preferred in these processes to employ hydrogen chloride in the feed with TCP, such appearing to favor the production of propylene over propane.

The present invention is more particularly illustrated by the examples which follow:

EXAMPLE 1

Calgon's BPLF3, coal-based activated carbon, having a specific surface area of 1100 $m^2/g$ to 1300 $m^2/g$, a pore volume of 0.7 to 0.85 $cm^3/g$, and an average pore radius of 12.3 to 14 angstroms, was impregnated to a loading of 0.5 weight percent of platinum using an aqueous chloroplatinic acid solution and an incipient wetness catalyst preparation technique.

This catalyst was dried in air at room temperature overnight and then calcined in an oven at 120 degrees Celsius for two hours.

A catalyst charge as thus prepared (approximately 1 gram) was then generally placed in a tubular reactor (comprised of Monel TM nickel alloy (unless specifically noted below all of the components, tubing and fittings of the test reactor apparatus were also made of Monel TM nickel alloy (Huntington Alloys, Inco Alloys International, Inc.), having a diameter (O.D.) of $\frac{1}{2}$ inch (1.27 cm), and being 12 inches (30.5 cm) in length and located within an aluminum block heated by a cartridge heater and regulated via a computer to maintain a selected reaction temperature of 220 degrees Celsius) over a glass wool support contained in the center of the reactor tubing.

The catalyst was then covered with a plug of glass wool and dried for 1 hour at 120 degrees Celsius under a nitrogen purge. The catalyst was then reduced by passing hydrogen through the reactor, while ramping the temperature upwards from 120 degrees to 220 degrees Celsius over a period of 2 hours. The reaction temperature of 220 degrees Celsius was achieved, and the reaction temperature and hydrogen gas flow were allowed to equilibrate for about 1 hour before liquid TCP (1,2,3-trichloropropane) feedstock flow was started into the apparatus.

In each instance, liquid TCP was pumped via a high pressure syringe pump through 1.6 mm (O.D.) (1/16 inch) Monel$^{TM}$ nickel alloy tubing into a packed sample cylinder serving as a feed evaporator.

The 1/16th inch tubing extended almost to the center of the packed cylinder, which was heated to a vaporizing temperature of 180 degrees Celsius using electrical heat tracing. Vaporization of the TCP feedstock was accomplished in the feed line, so that the TCP was superheated when combined with the hydrogen feed stream. Thermocouples were used to monitor the skin temperature of the feed evaporator and the temperature of the gas exiting the feed evaporator, and the temperature of the feed evaporator was controlled by computer.

The hydrogen feed stream was metered (at a 3 to 1 molar ratio of hydrogen to TCP for Example 1) to a preheater using a Model 8249 linear mass flow controller from Matheson Gas Products, Inc. Secaucus, N.J., with the preheater consisting of a packed sample cylinder wrapped with electrical heat tracing. Thermocouples were used to monitor both the skin temperature of the preheater and the temperature of the gas exiting the preheater. The preheater temperature was set and maintained at 140 degrees Celsius.

Vaporized TCP exiting the evaporator was mixed with the hydrogen gas from the preheater in a 2 foot (0.61 meter) long section of $\frac{1}{4}$ inch (0.64 cm) tubing maintained at a temperature of 140 degrees Celsius. The mixed gases then were passed into and reacted within the tubular reactor at the aforementioned reaction temperature of 220 degrees Celsius, under essentially atmospheric pressure (1 psig), with a 3:1 molar feed ratio of hydrogen to TCP and a 1 second residence time for a liquid hourly space velocity (LHSV) of 4.8.

After reacting the TCP and hydrogen in the vapor phase in the tubular reactor thus prepared, the products from the reaction were passed to a gas sampling valve, which provided gaseous aliquots for online gas chromatographic analysis in a Hewlett-Packard Model 5890 Series II gas chromatograph (Hewlett-Packard Company). The gas chromatograph was equipped with a flame ionization detector, and used 30 meter by 0.53 millimeter (I.D.) 100 percent methyl silicone/fused silica and 30 meter by 0.53 millimeter (I.D.) porous polymer-lined fused silica columns to separate the various reaction products. Response factors were conventionally determined by injections of gravimetrically-prepared standards of the individual reaction products. These response factors were applied in conjunction with individual peak areas and the total mols of all reaction products to determine the mol percents of individual components in the reactor effluent, and the selectivity to individual reaction products.

Under the aforementioned conditions, it was found that 93 percent of the TCP was converted to reaction products including propylene (12 percent selectivity) and propane (88 percent selectivity). After 100 hours of run time, no measurable deactivation of the catalyst was noted.

EXAMPLES 2 AND 3

The same apparatus, procedure and catalyst were used as in Example 1, but at a hydrogen to TCP molar feed ratio of 1:1 rather than 3:1, and at a residence time of 3.5 seconds versus 1 second in Example 1. Example 2 (1.4 LHSV) was conducted again at essentially atmospheric pressure (1 psig) with the results that 42 percent of the TCP was converted to reaction products including propylene (67 percent selectivity) and propane (32 percent selectivity). Example 3 was conducted at 10 psig and an LHSV of 2.3, and converted 42 percent of the TCP to propylene (44 percent selectivity) and propane (54 percent selectivity). Example 2 was continued over a period in excess of 250 hours with a deactivation rate of 0.001 percent conversion loss per hour.

What is claimed is:

1. A process for hydrodechlorinating 1,2,3-trichloropropane to produce propylene in preference to propane and in a yield of at least about 10 percent, comprising reacting 1,2,3-trichloropropane and hydrogen in the presence of a catalyst which consists of platinum in elemental or compound form on a support, under effective hydrodechlorinating conditions.

2. A process as defined in claim 1, wherein propylene is produced in a yield of at least about 20 percent.

3. A process as defined in claim 2, wherein propylene is produced in a yield of at least about 30 percent.

4. A process as defined in claim 1, wherein the support is carbon.

5. A process as defined in claim 1, wherein the process is conducted in the gas phase at a pressure of about 1000 psig or less, a hydrogen to 1,2,3-trichloropropane molar feed ratio of about 10 to 1 or less, a temperature of from about 25 degrees Celsius to about 400 degrees Celsius, and a residence time of from about 0.1 seconds to about 7,200 seconds.

6. A process as defined in claim 5, wherein the process is conducted in the gas phase at a pressure of about 250 psig or less, a hydrogen to 1,2,3-trichloropropane molar feed ratio of about 5 to 1 or less, a temperature of from about 150 degrees Celsius to about 350 degrees Celsius, and a residence time of from about 0.1 seconds to about 30 seconds.

7. A process as defined in claim 6, wherein the process is conducted in the gas phase at a pressure of about 100 psig or less, a hydrogen to 1,2,3-trichloropropane molar feed ratio of about 1 to 1 or less, a temperature of from about 150 degrees Celsius to about 250 degrees Celsius, and a residence time of from about 0.5 seconds to about 20 seconds.

8. A process as defined in any of claims 1-7, further comprising exposing the catalyst to a chloride source before contacting the catalyst with 1,2,3-trichloropropane and hydrogen.

9. A process as defined in claim 8, further comprising incorporating hydrogen chloride in the feed to the process.

* * * * *